US 6,610,473 B1

(12) United States Patent
Butz et al.

(10) Patent No.: US 6,610,473 B1
(45) Date of Patent: Aug. 26, 2003

(54) PEPTIDES FOR INHIBITING HPV E6-PROTEINS

(75) Inventors: Karin Butz, Hirschberg (DE); Felix Hoppe-Seyler, Heidelberg (DE)

(73) Assignee: Deutsches Krebsforschungszentrum Stiftung des Oeffentlichen Rechts, Heidelberg (DE)

(*) Notice: Subject to any disclaimer, the term of this patent is extended or adjusted under 35 U.S.C. 154(b) by 0 days.

(21) Appl. No.: 09/889,136

(22) PCT Filed: Jan. 12, 2000

(86) PCT No.: PCT/DE00/00141

§ 371 (c)(1),
(2), (4) Date: Oct. 4, 2001

(87) PCT Pub. No.: WO00/42064

PCT Pub. Date: Jul. 20, 2000

(30) Foreign Application Priority Data

Jan. 13, 1999 (DE) .......................... 199 01 008

(51) Int. Cl.[7] .................. C12Q 1/70; G01N 33/53; C12P 21/04; A61K 39/42; C07H 21/04
(52) U.S. Cl. ................. 435/5; 435/6; 435/7.1; 435/69.7; 424/159.1; 424/192.1; 424/199.1; 424/204.1; 536/23.1; 536/29.72
(58) Field of Search .............. 435/5, 6, 7.1, 69.7; 424/159.1, 192.1, 199.1, 204.1; 536/23.1, 23.72

(56) References Cited

U.S. PATENT DOCUMENTS 5,532,348 A 7/1996 Huibregtse et al. ........ 536/23.5

FOREIGN PATENT DOCUMENTS

| EP | 0 531 080 A2 | 3/1993 |
| WO | WO 96/02000 A1 | 1/1996 |
| WO | WO 97/18309 A1 | 5/1997 |

OTHER PUBLICATIONS

Philip James et al., "Genomic Libraries and a Host Strain Designed for Highly Efficient Two–Hybrid Selection in Yeast", Genetics, Dec., 1996, pp. 1425–1436, vol. 144, Genetics Society of America.

Marc Vidal et al., "Reverse two–hybrid and one–hybrid systems to detect dissociation of protein–protein and DNA–protein interactions", Proc. Natl. Acad. Sci. USA, Sep. 1996, pp. 10315–10320, vol. 93.

Primary Examiner—Hankyel T. Park
(74) Attorney, Agent, or Firm—Heller Ehrman White and McAuliffe (57) ABSTRACT

The present invention relates to peptides suited for inhibiting HPV-E6 proteins, DNAs encoding them and the use of both, particularly for eliminating HPV tumor cells.

26 Claims, 2 Drawing Sheets

SEQUENCE LISTING

<160> NUMBER OF SEQ ID NOS: 17

<210> SEQ ID NO 1
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 1

Gly Ala Leu Val His Lys Leu Phe Ser Gln Thr Ser Gly Ser Cys Leu
1               5                   10                  15

Val Cys Ile Ser
            20

```
<210> SEQ ID NO 2
<211> LENGTH: 19
<212> TYPE: PRT
<213> ORGANISM: Artificial Sequence
<220> FEATURE:
<223> OTHER INFORMATION: Peptide for inhibiting HPV-E6 protein

<400> SEQUENCE: 2

Leu Asp Val Leu Gly Cys Leu Val Arg Arg Leu Gly Val Val Leu Val
 1               5                  10                  15

Gly Leu His

<210> SEQ ID NO 3
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 3

Cys Tyr Val Glu Cys Gly Cys Glu Val Leu Thr Ala Leu Val Asn Gly
 1               5                  10                  15

Val Arg Val Leu
            20

<210> SEQ ID NO 4
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 4

Gly Val Gly Gly Leu Cys Ser Cys Ala Ser Cys Val Ser Glu Asp Phe
 1               5                  10                  15

Tyr Ala Ser Val
            20

<210> SEQ ID NO 5
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 5

Ile Asp Leu Leu Arg Arg Leu Gly Ser Gln Leu His Leu Leu Leu Val
 1               5                  10                  15

Ser Val Gly Gly
            20

<210> SEQ ID NO 6
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 6

Leu Ala Val Leu Leu Asn Gly Tyr Thr Arg Ala Ile Val Gly Ile Ser
 1               5                  10                  15

Phe Gly Gly Trp
            20
```

```
<210> SEQ ID NO 7
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 7

Leu Cys Thr Met Cys Ala Thr Val Phe Arg Pro Leu Val Trp Phe
1               5                   10                  15

Trp Ser Ile Trp
            20

<210> SEQ ID NO 8
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 8

Gln Leu Leu Leu Asp Leu Leu Leu Gly Ser Tyr Glu Gly Met Ser Leu
1               5                   10                  15

Thr Ser Ser Pro
            20

<210> SEQ ID NO 9
<211> LENGTH: 16
<212> TYPE: PRT
<213> ORGANISM: Artificial Sequence
<220> FEATURE:
<223> OTHER INFORMATION: Peptide for inhibiting HPV-E6 protein

<400> SEQUENCE: 9

Ser Arg Ser Asn Ala Leu His Thr Leu Asp Val Leu Leu Gly Gly Thr
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 10

Gly Gly Ala Val Tyr Leu Cys Asp Ala Gly Cys Cys Phe Tyr Cys Cys
1               5                   10                  15

Gly Cys Ser Gly
            20

<210> SEQ ID NO 11
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 11

Cys Leu Glu Leu Phe Asp Asp Leu Phe Leu Ala Leu Ser Leu Leu Leu
1               5                   10                  15

Leu Val Gly Gly
            20

<210> SEQ ID NO 12
<211> LENGTH: 19
```

```
<212> TYPE: PRT
<213> ORGANISM: Artificial Sequence
<220> FEATURE:
<223> OTHER INFORMATION: Peptide for inhibiting HPV-E6 protein

<400> SEQUENCE: 12

Pro Leu Cys Arg Thr Cys Leu Ile Glu Ser Ala Val Leu Ile Gln Leu
1               5                   10                  15

Ser Arg Leu

<210> SEQ ID NO 13
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 13

Val Phe Ser Gly Val Tyr Tyr Ala Glu Phe Val Phe Ala Ala Ser Ala
1               5                   10                  15

Gly Gly Thr Pro
            20

<210> SEQ ID NO 14
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 14

Met Ala Pro Val Gly Ala Gly Arg Pro Cys Cys Thr Val Cys Phe Leu
1               5                   10                  15

Thr Ala Arg Phe
            20

<210> SEQ ID NO 15
<211> LENGTH: 20
<212> TYPE: PRT
<213> ORGANISM: Artificial Sequence
<220> FEATURE:
<223> OTHER INFORMATION: Peptide for inhibiting HPV-E6 protein

<400> SEQUENCE: 15

Leu Ser Met Leu Leu Phe Ala Ala Lys Leu Pro Val Ala Val Leu Cys
1               5                   10                  15

Ser Trp Gln Ala
            20

<210> SEQ ID NO 16
<211> LENGTH: 19
<212> TYPE: PRT
<213> ORGANISM: Artificial Sequence
<220> FEATURE:
<223> OTHER INFORMATION: Peptide for inhibiting HPV-E6 protein

<400> SEQUENCE: 16

Leu Val Gly Arg Val Arg Ile Gly Val Ser Val Phe Ile Arg Gly Gly
1               5                   10                  15

Arg Leu Leu

<210> SEQ ID NO 17
<211> LENGTH: 20
<212> TYPE: PRT
```

-continued

```
<213> ORGANISM: Artificial Sequence
<220> FEATURE:
<223> OTHER INFORMATION: Peptide for inhibiting HPV-E6 protein

<400> SEQUENCE: 17

Leu Phe Asp Ile Phe Arg Leu Cys Ala Gln Pro Val Leu Val His Gly
1               5                   10                  15

His Thr Arg Val
            20
```

PEPTIDES FOR INHIBITING HPV E6-PROTEINS

The present invention relates to peptides which are suited to inhibit HPV-E6 proteins, DNAs coding for them and the use of both, particularly for eliminating HPV-positive cells, e.g. HPV tumor cells.

Human papilloma viruses (HPVs) are closely related with the development of carcinomas. The involvement of HPVs in the development of the cervical carcinoma is well characterized, and various findings refer to the fact that HPVs play a causal part in the etiology of this carcinoma. On a molecular level, sequences of HPVs, particularly HPV 16 and 18, are detectable in about 95% of the cervical carcinoma biopsies. In this connection, the HPV DNA is usually present in integrated form in the genome of the tumor cells. It frequently comprises deletions and/or rearrangements, which never refer to the early HPV genes, namely the E6 and E7 genes. These genes code for the HPV proteins E6 and E7 which are responsible for the formation and manifestation of HPV carcinomas. In this connection, the HPV proteins have a synergistic effect. On the other hand, there are references to the effect that they also display opposite activities. For example, the E7 protein induces apoptosis, whereas the E6 protein inhibits it. This is due to the fact that the E6 protein binds to p53 directly or indirectly, i.e. via ubiquintin-protein ligase E6-AP, and inhibits it, so that p53 can no longer display its apoptosis-inducing activity. The E6 protein also has an anti-apoptotic activity independent of p53. The genes of the E6 and E7 proteins are expressed via polycistronic mRNAs, the transcription being controlled by a common promoter. Experiments of inhibiting the latter and/or E6-/E7 mRNAs are known. These experiments resulted in a parallel inhibition of the growth of HPV tumor cells. However, elimination of such cells, which is most desired, could not be achieved by this.

Therefore, it is the object of the present invention to provide a product by which HPV tumor cells can be eliminated.

According to the invention this is achieved by the subject matters defined in the claims.

The applicant found that HPV-E6 proteins bind to short peptides. He screened a randomized oligopeptide library which comprises randomly generated peptide sequences with a "peptide aptamer system" in which the HPV-E6 protein was used as a screening sample. He found that short peptides, particularly those listed in Table 1, bind HPV-E6 proteins. He also found that these peptides are suited to inhibit activities of HPV-E6 proteins, e.g. their anti-apoptotic activity. In addition, he observed that an elimination of HPV-positive cells, particularly HPV tumor cells, can be achieved by this inhibition.

According to the invention, the applicant's insights are used to provide a peptide which is selected from the peptides listed in Table 1, wherein the peptide may comprise a sequence modification of up to 40%, particularly 20% and most particularly 10%.

| | |
|---|---|
| E61-1.pep: | NH$_2$-GALVHKLFSQ TSGSCLVCIS-COOH (SEQ ID NO: 1) |
| E61-2.pep: | NH$_2$-LDVLGCLVRR LGVVLVGLH-COOH (SEQ ID NO: 2) |
| E61-3.pep: | NH$_2$-CYVECGCEVL TALVNGVRVL-COOH (SEQ ID NO: 3) |
| E61-5.pep: | NH$_2$-GVGGLCSCAS CVSEDFYASV-COOH (SEQ ID NO: 4) |
| E61-7.pep: | NH$_2$-IDLLRRLGSQL HLLLVSVGG-COOH (SEQ ID NO: 5) |
| E61-8.pep: | NH$_2$-LAVLLNGYTR AIVGISFGGW-COOH (SEQ ID NO: 6) |
| E61-9c.pep: | NH$_2$-LCTMCATVFR PLLVWFWSIW-COOH (SEQ ID NO: 7) |
| E61-10.pep: | NH$_2$-QLLLDLLLGS YEGMSLTSSP-COOH (SEQ ID NO: 8) |
| E61-11.pep: | NH$_2$-SRSNALHTLD VLLGGT-COOH (SEQ ID NO: 9) |
| E61-12.pep: | NH$_2$-GGAVYLCDAG CCFYCCGCSG-COOH (SEQ ID NO: 10) |
| E61-13.pep: | NH$_2$-CLELFDDLFL ALSLLLLVGG-COOH (SEQ ID NO: 11) |
| E61-14.pep: | NH$_2$-PLCRTCLIES AVLIQLSRL-COOH (SEQ ID NO: 12) |
| E61-15.pep: | NH$_2$-VFSGVYYAEF VFAASAGGTP-COOH (SEQ ID NO: 13) |
| E61-16.pep: | NH$_2$-MAPVGAGRPC CTVCFLTARF-COOH (SEQ ID NO: 14) |
| E61-17.pep: | NH$_2$-LSMLLFAAKL PVAVLCSWQA-COOH (SEQ ID NO: 15) |
| E61-19.pep: | NH$_2$-LVGRVRIGVS VFIRGGRLL-COOH (SEQ ID NO: 16) |
| E61-20.pep: | NH$_2$-LFDIFRLCAQ PVLVHGHTRV-COOH (SEQ ID NO: 17) |

Peptides according to the invention are suited to bind HPV-E6 proteins and inhibit them as regards their activities, e.g. as regards their anti-apoptotic activity.

The expression "HPV-E6 proteins" comprises an E6 protein of any HPV type, particularly of HPV1, 5, 6, 11, 16, 18, 31, 33 or 35. An E6 protein can have a wild-type sequence or a sequence differing therefrom by one or several amino acids. Furthermore, it may be present in shortened form, i.e. it is only available as the fragment which is necessary to bind to p53, ubiquintin-protein ligase E6-AP or another binding participant of the E6 protein. The fragment can also be present in multiple copies within a polypeptide molecule. An E6 protein or a fragment thereof can also be present in the form of a fusion protein.

Peptides according to the invention can be provided by common methods in which peptides are tested as regards their binding to HPV-E6 proteins. Such methods are e.g. the "peptide aptamer" or "bacteriophage display" method. It is favorable to use the "peptide aptamer" method which is described in the examples and which is a modification of the above-mentioned method.

Peptides according to the invention can be present as such or in combination with other substances, e.g. (poly) peptides. The combination may consist in linking the peptides according to the invention with the (poly)peptides via linkers, e.g. disulfide bridges. The peptides according to the invention can also be fused with the (poly)peptides, so that the peptides according to the invention are present in the form of fusion (poly)peptides. For example, leader peptides, such as penetratin from *Drosophila antennapedia* or VP22 from HSV1, which support the absorption of the peptides according to the invention in cells, offer themselves as (poly)peptides for fusion (poly)peptides. On the other hand, polypeptides which are linked with the peptide according to the invention via linkers, can be e.g. carrier proteins, such as transferrin, which are not considered foreign by the body. Several peptides according to the invention can also be simultaneously present in combination with an above-mentioned substance.

A further subject matter of the present invention relates to a nucleic acid, particularly a DNA which codes for a peptide according to the invention. Such a DNA can be present in vectors, particularly expression vectors. A person skilled in the art is familiar with examples thereof. In the case of an expression vector for *E. coli*, these are e.g. pGEMEX, pUC derivatives, pGEX-2T, pET3b and pQE-8. For the expression in yeast, e.g. pY100 and Ycpad1 have to be mentioned while e.g. pKCR, PEFBOS, cDM8 or pCEV4 have to be indicated for the expression in animal cells. The baculovirus expression vector pAcSGHisNT-A is especially suited for the expression in insect cells. It is also possible to use viruses, e.g. adenovirus, vaccinia virus, adeno-associated virus (AAV) or retroviruses, such as MoMuLV, HaMuSV, MuMTV, RSV or GaIV, for the expression in animal cells.

The person skilled in the art is familiar with suitable cells to express a DNA according to the invention, which is present in an expression vector. Examples of such cells comprise the *E. coli* strains HB101, DH1, x1776, JM101, JM109, BL21 and SG13009, the yeast strain *Saccharomyces cerevisiae* and the animal cells L, NIH 3T3, FM3A, CHO, COS, Vero and HeLa as well as the insect cells sf9.

The person skilled in the art knows in which way the DNA according to the invention has to be inserted in an expression vector. He is also familiar with the fact that this DNA can be inserted in combination with a DNA coding for another peptide or polypeptide, so that the DNA according to the invention can be expressed in the form of a fusion polypeptide.

In addition, the person skilled in the art knows conditions of culturing transformed or transfected cells. He is also familiar with methods of isolating and purifying the peptide or fusion polypeptide, which is expressed by the DNA according to the invention.

A further subject matter of the present invention relates to an antibody directed against an above peptide or fusion polypeptide. Such an antibody can be prepared by common methods. It may be polyclonal or monoclonal. For its preparation it is favorable to immunize animals—particularly rabbits or chickens for a polyclonal antibody and mice for a monoclonal antibody—with an above (fusion) polypeptide or with fragments thereof. Further "boosters" of the animals can be effected with the same (fusion) polypeptide or with fragments thereof. The polyclonal antibody may then be obtained from the animal serum or egg. For the preparation of the monoclonal antibody, animal spleen cells are isolated and fused with myeloma cells.

A further subject matter of the present invention relates to a pharmaceutical composition which contains one or several peptides according to the invention and/or DNAs encoding them as well as conventional auxiliary agents. The auxiliary agents used can be e.g. carriers, binders, blasting agents, lubricants, solvents, solution aids, release accelerators, release retarders, emulsifiers, stabilizers, etc. Such a composition can be used as usual, e.g. orally or parenterally. The suitable dosage is determined in the individual case as usual.

A further subject matter of the present invention relates to a diagnostic composition which contains one or several peptides according to the invention. HPV-E6 proteins can be detected by such a composition. This can be used to detect HPV-associated diseases, such as HPV infections, HPV dysplasias of HPV carcinomas. Such a detection comprises e.g. (a) collection of a cell sample from a patient, (b) contacting of the cell sample with a peptide according to the invention under conditions permitting the specific binding of the peptide to an HPV-E6 protein, and (c) detection of the peptide. This detection can be made by standard methods. For example, the peptides according to the invention can be present in the liquid phase or be bound to a solid carrier and be labeled in different ways. The person skilled in the art is familiar with suitable markers and labeling methods. The peptides can also be detected by antibodies according to the invention. The latter are also suited to control the therapeutic course of an HPV-associated disease treated with peptides according to the invention.

By means of the present invention it is possible to bind HPV-E6 proteins and inhibit their activities, particularly their anti-apoptotic activity. This serves for achieving the elimination of HPV-positive cells, particularly HPV tumor cells. HPV-positive cells can also be diagnosed. Therefore, the present invention is suitable to take diagnostic and therapeutic steps against HPV-associated diseases, particularly HPV infections, HPV dysplasias or HPV carcinomas. In addition, the peptides according to the invention and/or DNAs encoding them represent a basis for the development of fully new active substances against the above diseases.

BRIEF DESCRIPTION OF THE DRAWINGS

FIG. 1 shows the modified "peptide aptamer" system in *S. cerevisiae* by way of diagram. This system comprises three components: (1) the target protein (E6) which is fused with a heterologous DNA binding domain (GAL4BD), (2) a peptide having randomized amino acid sequence, which is fused to a transcriptional activation domain (GAL4AD), and (3) a stably integrated selection gene (prototrophic selection markers, such as ADE2), which has the recognition sequence for the DNA binding domain in its promoter. A synthetic transcription factor forms by interaction between peptide and target protein. It binds to the recognition sequence in the promoter region of the selection gene by the transactivation domain and stimulates the transcription of the selection gene by the transactivation domain. Under selection conditions (e.g. adenine-negative media) only the yeast cells form colonies which express a peptide with affinity for the target protein (TrxA=i E. colithioreduxin A; TAG=influenza virus HA-Tag; NLS=nuclear localization signal).

FIG. 2 shows the analysis of HPV16-E6-binding peptides in the "peptide aptamer" system. By screening about $2 \times 10^6$ yeast cells, 15 positive clones are isolated (cf. Table 1, E61-1.pep–E61.-17.pep). Replica platings of the yeast colonies (master plate above: 1–15=positive clones; K=randomly selected control clone) are carried out under selection for ADE 2(GAL4-BS in context of the GAL2 promoter), HIS3 (GAL4BS on the basis of the GAL1 promoter) and URA3 (GAL4-BS on the basis of the SPO13 promoter).

The following examples explain the invention.

EXAMPLE 1

Screening for HPV-E6 Protein-binding Peptides

Figure 1:
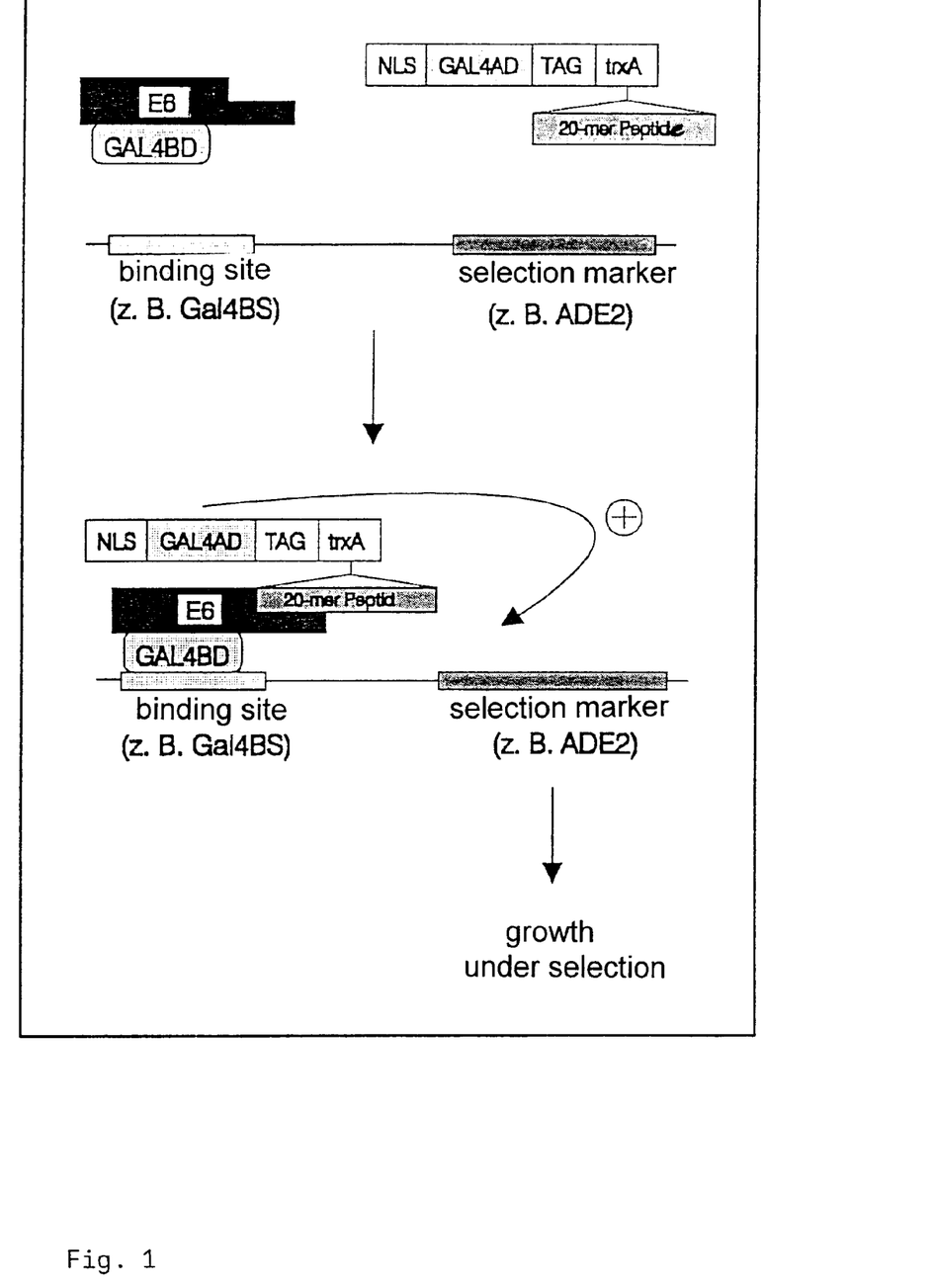

A method is used which is derived from the known "peptide aptamer" system. The method is shown in FIG. 1 by way of diagram.

For the screening for HPV-E6 protein-binding peptides, a randomized oligopeptide expression library is established for 20 amino acid-long peptides having random sequence (complexity about $2 \times 10^8$ differing peptides). Codons are defined by the sequence NNK (N=G, A, T or C; K=G or C). They code for all of the 20 amino acids, but only result in one stop codon. A yeast expression vector, pADTrx, is used as the expression vector. It contains *E. coli* Trx A (thioreduxin protein) from pTrx (Invitrogen company) and GAL4AD as well as the ADH promoter from pAS2 and/or pGAD424 (Clontech company). The peptides are expressed on the basis of the active loop of Trx. This comprises the following advantages:

- the presentation of the peptides outwards is ensured on the basis of the Trx loop,
- conformally restricted peptides can expose amino acids outwards which are possibly folded inwards in flexible peptides in the intracellular environment,
- conformally restricted peptides can be highly affine peptides, which have the potential of acting as efficient protein inhibitors in vivo as well.

A yeast strain, KF-1, is also used. It originates from the yeast strain PJ69-4A (cf. James et al., Genetics 144 (1996), 1425) and permits the analysis of three selection markers: ADE2, HIS3 and URA3. Each of the three selection markers is under the transcriptional control of GAL4 binding sites on the basis of various promoters. The URA3 selection marker is regulated by the SPO13 promoter which originates from the yeast strain MaV103 (cf. Vidal et al., Proc. Natl. Acad. Sci. USA (93), 10315–10320), contains a negatively regulatory element and can be activated by strong protein-protein interactions. The yeast strain also contains the $E.\ coli$ β-galactosidase (-Gal) gene as further marker, whose activity can easily be quantified and enables an evaluation of the in vivo binding activity of the peptide to the E6 protein. The activation of the HIS3 gene can also be quantified by titration using 3'AT-(3-amino-1, 2, 4-triazole).

Figure 2:
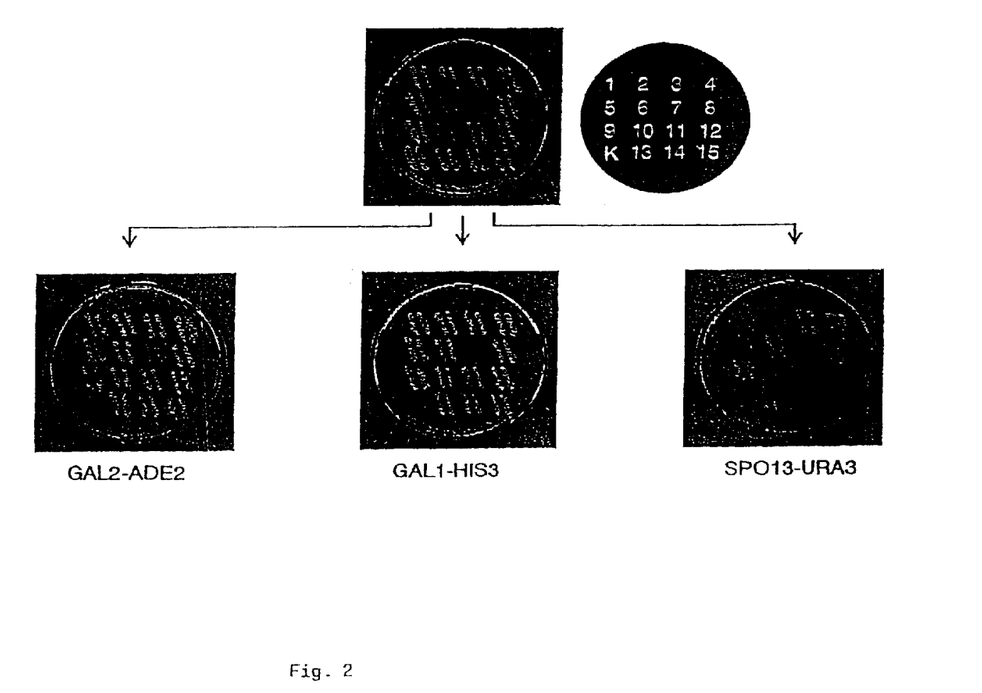

The HPV16-E6 protein is subjected to screening using the above system. For this purpose, it is provided in the form of an expression vector coding for it. pPC97 (cf. Vidal et al., above) serves as a basic vector in which the coding sequence of an HPV16-E6 protein is inserted. 15 clones are isolated from about $2 \times 10^6$ yeast clones, which show growth under ADE2 selection. Replica platings and the analysis of the three selection markers reveal that 14 of the 15 clones show growth also under HIS3 selection (FIG. 2). In addition, 6 of the isolated clones show additionally growth under URA3 selection, which refers to an especially high in vivo affinity of the corresponding peptide for the HPV-E6 protein under the conditions employed herein.

For further control the corresponding peptide expression plasmids are isolated from the 15 clones and subjected to rescreening in yeast after another transformation. The rescreening shows a complete conformity with the results from the above replica platings (FIG. 2). It turns out that the growth of the yeast depends on the binding of the peptides to the HPV16-E6 protein.

The peptides of the 15 clones are determined as regards their amino acid sequence. It is indicated in Table 1, E61-1.pep–E61-17.pep. Part of the peptides show sequence homologies with the binding domains, related to one another, of the E6-binding proteins E6-AP, E6-BP and paxillin (LhXΦLs"-like motives, in which: h=Q, E or N; X=any amino acid; Φ=hydrophobic amino acid; s=small amino acid such as G or A and -=acidic amino acid). The other part of the E6-binding peptides have no obvious sequence similarities with respect to the above E6-binding proteins. However, their sequences can give references to formerly unknown E6 interaction participants.

In another screening assay, two further clones are obtained. Their amino acid sequence is indicated in Table 1, E61-19.pep and E61-20.pep.

EXAMPLE 2

Inhibition of the Anti-apoptotic Activity of HPV-E6 Proteins by Peptides According to the Invention The "VP 22 shuttle system" is used. It is based on the fact that the HSV1-VP 22 protein is absorbed by cells, i.e. can be used as a carrier. Fusion polypeptides from VP 22 and peptides of Table 1 according to the invention are prepared. For this purpose, the expression vector pCEP4 (Invitrogen company) is used. The DNA sequences of the above peptides are inserted therein in phase with the DNA sequence of VP 22. In this connection, the peptides are expressed on the basis of the $E.\ coli$ TrxA protein. The resulting expression plasmids pCEP4/ E61-1.pep and/or pCEP4/E61-2.pep are transfected in HPV16-positive SiHa and/or CaSKi cervical carcinoma cells. The morphology of the cells and their growth is examined by common methods at various times.

It turns out that the anti-apoptotic activity of HPV-E6 proteins can be inhibited by the peptides according to the invention. Furthermore, it shows that the apoptosis induced by HPV-E7 proteins is obtained. This is also reflected in "colony formation assays" which show strong growth inhibition of the cells. Thus, a peptide according to the invention is suited to eliminate HPV-positive cells, particularly HPV tumor cells.

What is claimed is:

1. A peptide selected from the following peptides:
NH$_2$-GALVHKLFSQ TSGSCLVCIS-COOH (SEQ ID NO: 1)
NH$_2$-LDVLGCLVRR LGVVLVGLH-COOH (SEQ ID NO: 2)
NH$_2$-CYVECGCEVL TALVNGVRVL-COOH (SEQ ID NO: 3)
NH$_2$-GVGGLCSCAS CVSEDFYASV-COOH (SEQ ID NO: 4)
NH$_2$-IDLLRRLGSQL HLLLVSVGG-COOH (SEQ ID NO: 5)
NH$_2$-LAVLLNGYTR AIVGISFGGW-COOH (SEQ ID NO: 6)
NH$_2$-LCTMCATVFR PLLVWFWSIW-COOH (SEQ ID NO: 7)
NH$_2$-QLLLDLLLGS YEGMSLTSSP-COOH (SEQ ID NO: 8)
NH$_2$-SRSNALHTLD VLLGGT-COOH (SEQ ID NO: 9)
NH$_2$-GGAVYLCDAG CCFYCCGCSG-COOH (SEQ ID NO: 10)
NH$_2$-CLELFDDLFL ALSLLLLVGG-COOH (SEQ ID NO: 11)
NH$_2$-PLCRTCLIES AVLIQLSRL-COOH (SEQ ID NO: 12)
NH$_2$-VFSGVYYAEF VFAASAGGTP-COOH (SEQ ID NO: 13)
NH$_2$-MAPVGAGRPC CTVCFLTARF-COOH (SEQ ID NO: 14)
NH$_2$-LSMLLFAAKL PVAVLCSWQA-COOH (SEQ ID NO: 15)
NH$_2$-LVGRVRIGVS VFIRGGRLL-COOH (SEQ ID NO: 16)
NH$_2$-LFDIFRLCAQ PVLVHGHTRV-COOH and (SEQ ID NO: 17) and
a peptide containing a sequence modification of up to 40% thereof; wherein the peptide binds to HPV-E6 protein.

2. The peptide according to claim 1, wherein the peptide is present as a fusion polypeptide.

3. The peptide according to claim 2, wherein the fusion polypeptide comprises a leader sequence.

4. A DNA coding for the peptide according to claim 1.

5. An expression vector containing the DNA according to claim 4.

6. An antibody directed against the peptide according to claim 1.

7. A pharmaceutical composition comprising an auxiliary agent and a peptide selected from the following peptides:
NH$_2$-GALVHKLFSQ TSGSCLVCIS-COOH (SEQ ID NO: 1)
NH$_2$-LDVLGCLVRR LGVVLVGLH-COOH (SEQ ID NO: 2)
NH$_2$-CYVECGCEVL TALVNGVRVL-COOH (SEQ ID NO: 3)
NH$_2$-GVGGLCSCAS CVSEDFYASV-COOH (SEQ ID NO: 4)
NH$_2$-IDLLRRLGSQL HLLLVSVGG-COOH (SEQ ID NO: 5)
NH$_2$-LAVLLNGYTR AIVGISFGGW-COOH (SEQ ID NO: 6)
NH$_2$-LCTMCATVFR PLLVWFWSIW-COOH (SEQ ID NO: 7)
NH$_2$-QLLLDLLLGS YEGMSLTSSP-COOH (SEQ ID NO: 8)
NH$_2$-SRSNALHTLD VLLGGT-COOH (SEQ ID NO: 9)
NH$_2$-GGAVYLCDAG CCFYCCGCSG-COOH (SEQ ID NO: 10)
NH$_2$-CLELFDDLFL ALSLLLLVGG-COOH (SEQ ID NO: 11)
NH$_2$-PLCRTCLIES AVLIQLSRL-COOH (SEQ ID NO: 12)
NH$_2$-VFSGVYYAEF VFAASAGGTP-COOH (SEQ ID NO: 13)
NH$_2$-MAPVGAGRPC CTVCFLTARF-COOH (SEQ ID NO: 14)
NH$_2$-LSMLLFMKL PVAVLCSWQA-COOH (SEQ ID NO: 15)
NH$_2$-LVGRVRIGVS VFIRGGRLL-COOH (SEQ ID NO: 16)
NH$_2$-LFDIFRLCAQ PVLVHGHTRV-COOH and (SEQ ID NO: 17) and
a peptide containing a sequence modification of up to 40% thereof; wherein the peptide binds to HPV-E6 protein.

8. The composition according to claim 7, wherein the peptide is present as a fusion polypeptide.

9. The composition according to claim 8, wherein the fusion polypeptide comprises a leader sequence.

10. A method of treating a subject comprising administering to said subject a pharmaceutically effective amount of the peptide according to claim 1, wherein said peptide inhibits the function of said HPV-E6 protein.

11. The method according to claim 10, wherein the peptide eliminates HPV-positive cells.

12. The method according to claim 11, wherein the HPV-positive cells originate from an HPV-associated disease.

13. The method according to claim 12, wherein the HPV-associated disease is selected from the group consisting of an HPV infection, an HPV dysplasia, and an HPV carcinoma.

14. The method according to claim 10, wherein HPV is selected from the group consisting of HPV1, HPV5, HPV6, HPV11, HPV16, HPV18, HPV31, HPV33, and HPV35.

15. A DNA coding for the peptide according to claim 2.

16. A DNA coding for the peptide according to claim 3.

17. An antibody directed against the peptide according to claim 2.

18. An antibody directed against the peptide according to claim 3.

19. The peptide according to claim 1, which is selected from the following peptides:

NH$_2$-GALVHKLFSQ TSGSCLVCIS-COOH (SEQ ID NO: 1)

NH$_2$-LDVLGCLVRR LGVVLVGLH-COOH (SEQ ID NO: 2)

NH$_2$-CYVECGCEVL TALVNGVRVL-COOH (SEQ ID NO: 3)

NH$_2$-GVGGLCSCAS CVSEDFYASV-COOH (SEQ ID NO: 4)

NH$_2$-IDLLRRLGSQL HLLLVSVGG-COOH (SEQ ID NO: 5)

NH$_2$-LAVLLNGYTR AIVGISFGGW-COOH (SEQ ID NO: 6)

NH$_2$-LCTMCATVFR PLLVWFWSIW-COOH (SEQ ID NO: 7)

NH$_2$-QLLLDLLLGS YEGMSLTSSP-COOH (SEQ ID NO: 8)

NH$_2$-SRSNALHTLD VLLGGT-COOH (SEQ ID NO: 9)

NH$_2$-GGAVYLCDAG CCFYCCGCSG-COOH (SEQ ID NO: 10)

NH$_2$-CLELFDDLFL ALSLLLLVGG-COOH (SEQ ID NO: 11)

NH$_2$-PLCRTCLIES AVLIQLSRL-COOH (SEQ ID NO: 12)

NH$_2$-VFSGVYYAEF VFAASAGGTP-COOH (SEQ ID NO: 13)

NH$_2$-MAPVGAGRPC CTVCFLTARF-COOH (SEQ ID NO: 14)

NH$_2$-LSMLLFAAKL PVAVLCSWQA-COOH (SEQ ID NO: 15)

NH$_2$-LVGRVRIGVS VFIRGGRLL-COOH (SEQ ID NO: 16)

NH$_2$-LFDIFRLCAQ PVLVHGHTRV-COOH and (SEQ ID NO: 17).

20. A method of treating a subject comprising administering to said subject a pharmaceutically effective amount of the pharmaceutical composition according to claim 7, wherein said peptide of said pharmaceutical composition inhibits the function of an HBV-E6 protein.

21. A method for generating a peptide that binds to HPV-E6 protein, the method comprising the steps:
   a) generating multiple forms of peptides;
   b) testing for binding between the peptides and HPV-E6 protein; and
   c) determining the sequence of a tested peptide that binds to the HPV-E6 protein.

22. A method as described in claim 21, wherein the HPV protein is from HPV1, 5, 6, 11, 16, 18, 31, 33, or 35.

23. A method as described in claim 21, wherein the HPV protein is a fragment that binds p53 or ubiquitin-protein ligase E6-AP.

24. A method as described in claim 21, wherein the peptides are generated and displayed for binding to the HPV-E6 protein by a peptide aptamer or bacteriophage display method.

25. A peptide that binds to HPV-E6 protein, prepared by the method of claim 21.

26. A peptide that binds to HPV-E6 protein, prepared by the method of claim 22.

* * * * *